(12) United States Patent
Radzinsky

(10) Patent No.: US 8,646,733 B2
(45) Date of Patent: Feb. 11, 2014

(54) UNIVERSAL TUBE CLAMP

(75) Inventor: Vladimir Radzinsky, Beverly Hills, CA (US)

(73) Assignee: Vladimir Radzinsky, Torrance, CA (US)

(*) Notice: Subject to any disclaimer, the term of this patent is extended or adjusted under 35 U.S.C. 154(b) by 475 days.

(21) Appl. No.: 12/840,968

(22) Filed: Jul. 21, 2010

(65) Prior Publication Data

US 2012/0018594 A1    Jan. 26, 2012

(51) Int. Cl.
*F16B 2/08* (2006.01)

(52) U.S. Cl.
USPC .............................. 248/74.1; 403/290; 623/38

(58) Field of Classification Search
USPC ............... 248/74.1, 62, 230.1, 230.5, 313; 623/38, 27; 24/279, 280; D8/396; 285/154.3, 154.4, 403, 404, 420; 403/191, 290, 335, 338
See application file for complete search history.

(56) References Cited

U.S. PATENT DOCUMENTS

| | | | | |
|---|---|---|---|---|
| D123,589 S | * | 11/1940 | Eden | D13/120 |
| 4,442,994 A | * | 4/1984 | Logsdon | 248/547 |
| 4,565,464 A | * | 1/1986 | Nilsson | 403/290 |
| 4,660,870 A | * | 4/1987 | Donley | 285/419 |
| 5,319,995 A | * | 6/1994 | Huang | 74/551.8 |
| 5,482,234 A | * | 1/1996 | Lyon | 248/74.5 |
| 5,704,526 A | * | 1/1998 | Kuo | 224/425 |
| D396,801 S | * | 8/1998 | Petty | D8/356 |
| 5,988,727 A | * | 11/1999 | Mueller | 296/78.1 |
| 6,152,412 A | * | 11/2000 | Basickes et al. | 248/317 |
| D438,783 S | * | 3/2001 | Elliott | D8/396 |
| 6,716,104 B2 | * | 4/2004 | MacDonald | 464/89 |
| 7,762,246 B2 | * | 7/2010 | Telford | 124/49 |
| 2003/0220701 A1 | * | 11/2003 | Steinbarger et al. | 623/38 |
| 2006/0079965 A1 | * | 4/2006 | Benson | 623/38 |
| 2008/0298886 A1 | * | 12/2008 | Chen | 403/373 |
| 2009/0065659 A1 | * | 3/2009 | Dann | 248/74.1 |

* cited by examiner

*Primary Examiner* — Terrell McKinnon
*Assistant Examiner* — Ingrid M Weinhold
(74) *Attorney, Agent, or Firm* — Blue Capital Law Firm, P.C.

(57) ABSTRACT

A universal tube clamp, having a head portion with an aperture formed therein with set screws to retain another object thereto, and a clamping portion. The clamping portion has an outer perimeter sidewall defining an opening with knurls formed on inside walls, a generally T-shaped slot with a vertical portion that extends from a bottom of the sidewall upwardly towards the head portion with ears formed on both sides of the slot, and a horizontal slot portion that extends horizontally through the sidewall above the two ears, and a bolt which forces the two ears together to reduce a diameter of the opening. The ear that the bolt head impinges on is narrower than the threaded ear, and the vertical portion of the T-shaped slot is wider at the bottom of the sidewall than at its top where it joins the horizontal slot portion.

5 Claims, 21 Drawing Sheets

UNIVERSAL TUBE CLAMP

BACKGROUND OF THE INVENTION

The invention relates to tube clamps and tube clamp assemblies for use in prosthetic limbs. More particularly, the invention relates to a universal tube clamp and tube clamp assembly that are smaller, lighter, less expensive to manufacture, and more reliable than currently available tube clamps and tube clamp assemblies.

Prosthetic limbs are attached to the residual limb or stump by a stump socket, which is a shell that closely conforms to the residual limb. Attached to the stump socket is a threaded socket adaptor which is adapted to engage with an intermediate connector, such a pyramid plug. Some pyramid plugs have a base region in the general shape of a segment of sphere from the top of which extends a four sided frustum with the wider end at the top thereof. One such pyramid plug is shown in FIG. 22. Pyramid plugs are widely used in constructing prosthetics, and the frustum(s) of the pyramid plugs are adapted to adjustably engage with adapters and clamps to assemble prosthetics.

Multi-prong laminating adaptors are also used in the prosthetic industry in the creation of laminated stump sockets. The laminated stump socket is fit over the residual limb or stump of the patient, and is configured to allow the prosthetic device to be attached thereto via connection with the laminating adaptor.

Part of the skill of a prosthetist is in selecting the right combination of sizes, shapes, lengths and angles of the various components from different manufacturers in order to make a prosthetic that strong, reliable, and comfortable for a patient and that can be easily adjusted and stay in adjustment under regular and repeated use. Components that can be more easily and reliably used allow a prosthetist to do a better job with less time and improved patient satisfaction. For prosthetics that substitute for elongate limbs, such as the calves, thighs, etc., high strength tubes are commonly used with connectors at both ends. The tubes can be constructed out of material such as aluminum, steel, and composite materials such as carbon fiber, and the connectors, e.g., tube clamps and receivers, can be formed of high strength material such as aluminum, stainless steel, and titanium. While titanium is an ideal material for prosthetics since it is extremely strong and light, it is much more expensive than stainless steel and more difficult to machine. The tubes will come in a variety of diameters, wall thicknesses, materials, and lengths depending on the requirement, and the practitioner will cut the tube length to size to provide the needed length. Tube sizes which are commonly available to the industry include diameters of 22 mm, 25 mm, and 34 mm. The accepted "standard" size of a tube clamp is considered to be 30 mm. Depending on the manufacturer, the sizes and tolerances of the tubing can vary widely, so a tube from one manufacturer that is nominally 30 mm OD might be undersized by about 0.8 mm while a tube from another manufacturer may be oversized by about 0.8 mm. As a result, tube clamps and receivers are generally sized large to fix tube from different manufacturers. In order to provide for connection between tubes and other components of the prosthetic, the tube clamps and receivers are positioned on both ends of the tube. For speed and ease of assembly, tubes can be provided with a tube clamp or a receiver pre-affixed to one end of the tube. In prior art tube clamp assemblies, tubes of predetermined lengths, e.g., 20, 30, 40 cm, are provided with a receiver adhered to one end, e.g., such as by epoxy adhesive. The prosthetist will cut the second end of the tube to the required length and then attach a tube clamp to the second end of the tube. This second clamp is clamped on the second end of the tube by a screw that squeezes the tube clamp and secures it to the tube. Unfortunately, with repeated shock and possibly different coefficients of thermal expansion between the tube, which may be of one material, e.g., aluminum, and the tube clamps or receiver, which may be made of another material, e.g., stainless steel, aluminum alloy, titanium, for example, the adhesive bond between the first tube clamp or receiver and the tube can become compromised. If this occurs, the tube clamp or receiver can rotate relative to the tube, which will place the components out of alignment with each other. Moreover, with prior art clamps that are mechanically tightened with a screw, the second tube clamp can become loose on the tube and thereby allow rotation of the parts relative to each other, which is undesirable.

In the case of prior art titanium tube clamps, they are often formed by machining cylindrical stock. Due to the very high costs of titanium, designs that can reduce the amount of material required to form a tube clamp or receiver will result is great cost savings as well as weight savings, both of which are desirable.

Accordingly, there is a need for improved tube clamps and tube clamp assemblies.

SUMMARY OF THE INVENTION

The invention is a tube clamps and tube clamp assemblies for use in prosthetic limbs.

BRIEF DESCRIPTION OF THE DRAWINGS

FIG. 19 is a side view of the art tube clamp assembly of the invention with the exemplary receiver of FIG. 11 fixed to a first end of the tube and the exemplary tube clamp of FIG. 6 clamped to the second end of the tube.

DETAILED DESCRIPTION

Figure 1:
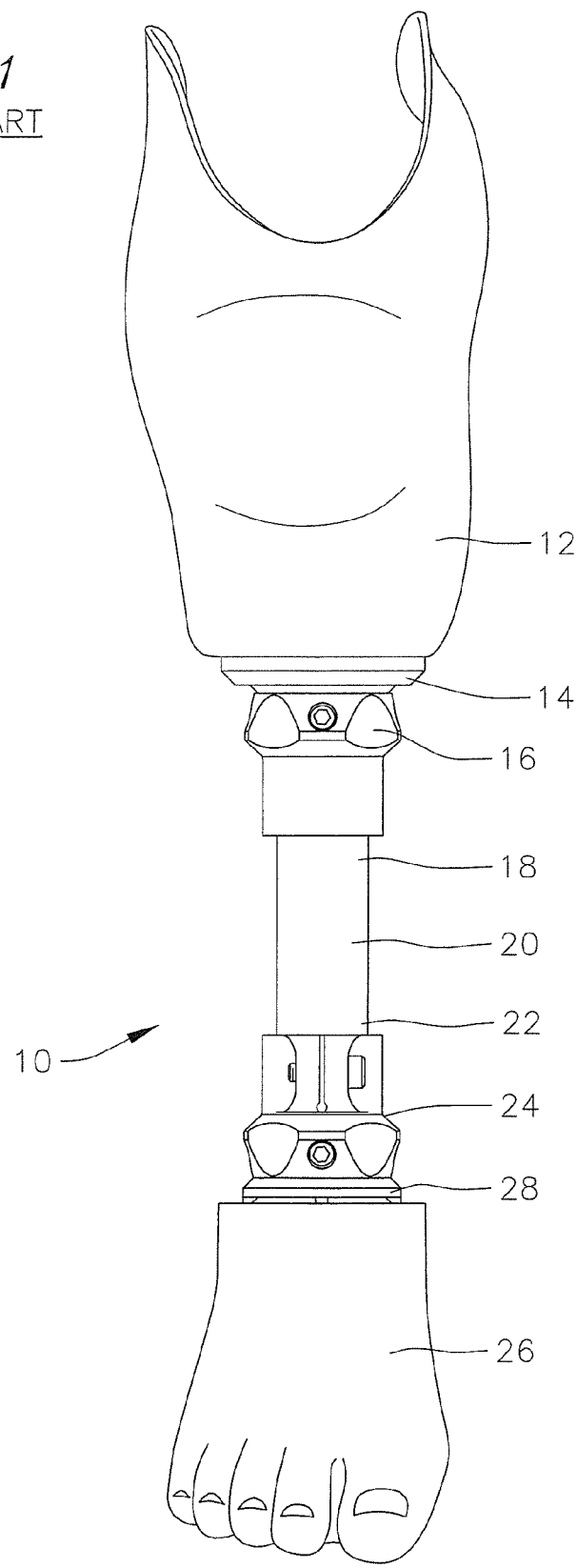
FIG. 1 is a perspective view of a typical prior art setup for a below the knee prosthetic.
Figure 22:
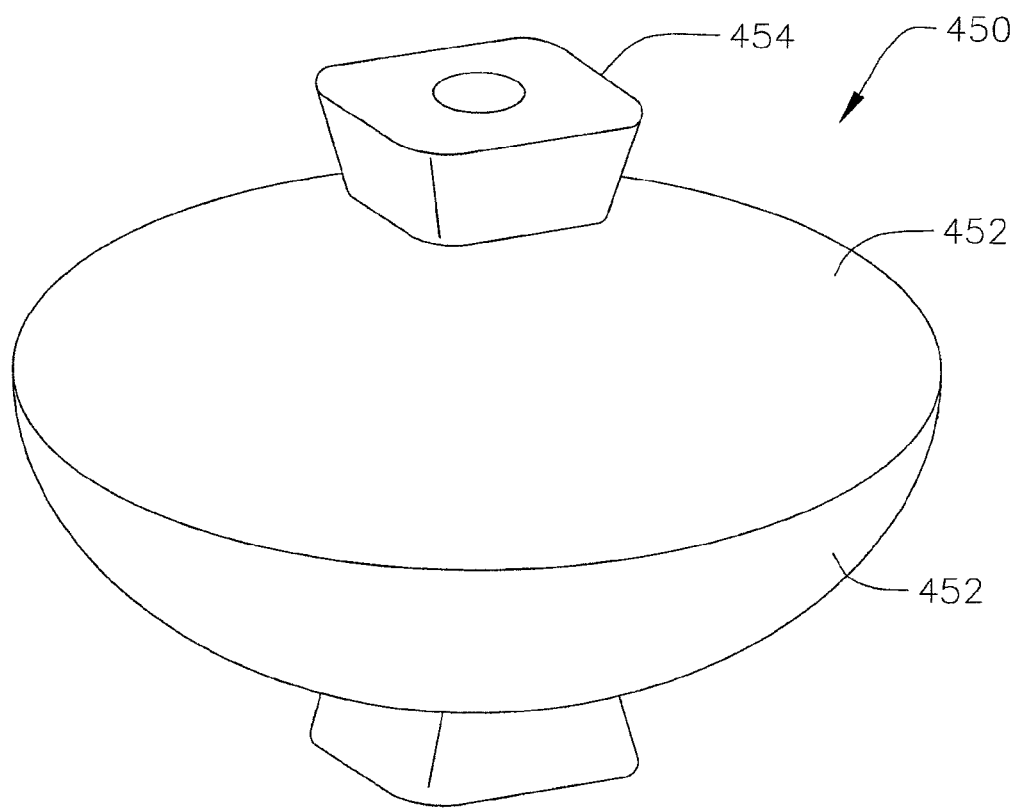
FIG. 22 is a perspective view of a prior art pyramid plug.

Turning first to FIG. 1, there is shown a perspective view of one typical setup for a below the knee prosthetic 10. A residual limb or stump socket 12 fits onto the patient's residual limb (not shown). The stump socket 12 has a socket adaptor 14 at a lower end, and is adapted to engage with an intermediate connector, such a pyramid plug, as shown in FIG. 22, but not revealed in this view. The pyramid plug connects the socket adaptor 14 to a prior art receiver 16, which is fitted on a first end 18 of a tube 20. At the second end 22 of the tube 20 a prior art tube clamp 24 is attached. The tube clamp 24 is in turn connected to a prosthetic foot 26 via a connector 28.

Figure 2:
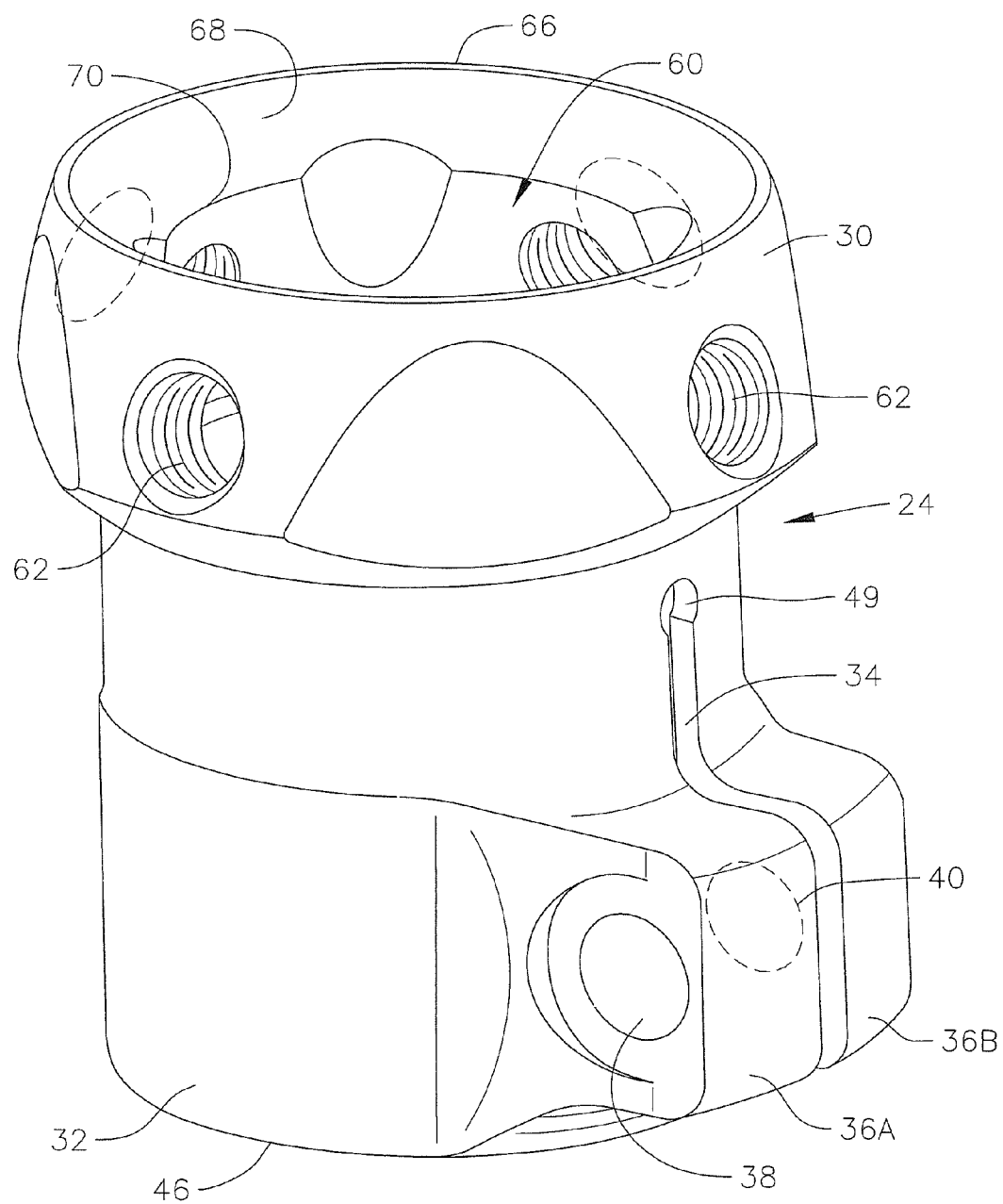
FIG. 2 is a perspective view of a prior art tube clamp.
Figure 3:
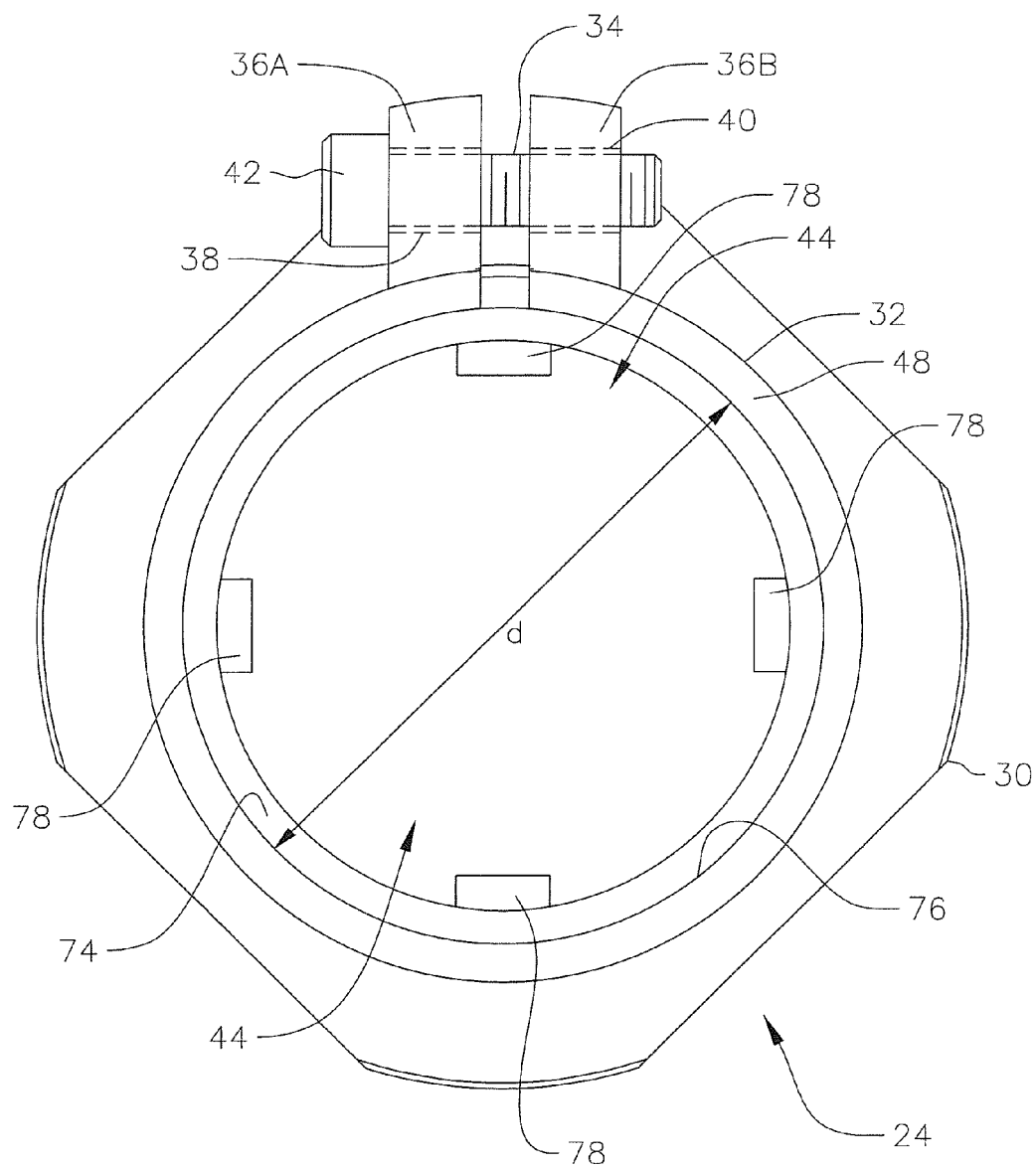
FIG. 3 is a bottom plan view of the prior art tube clamp of FIG. 2.
Figure 18:
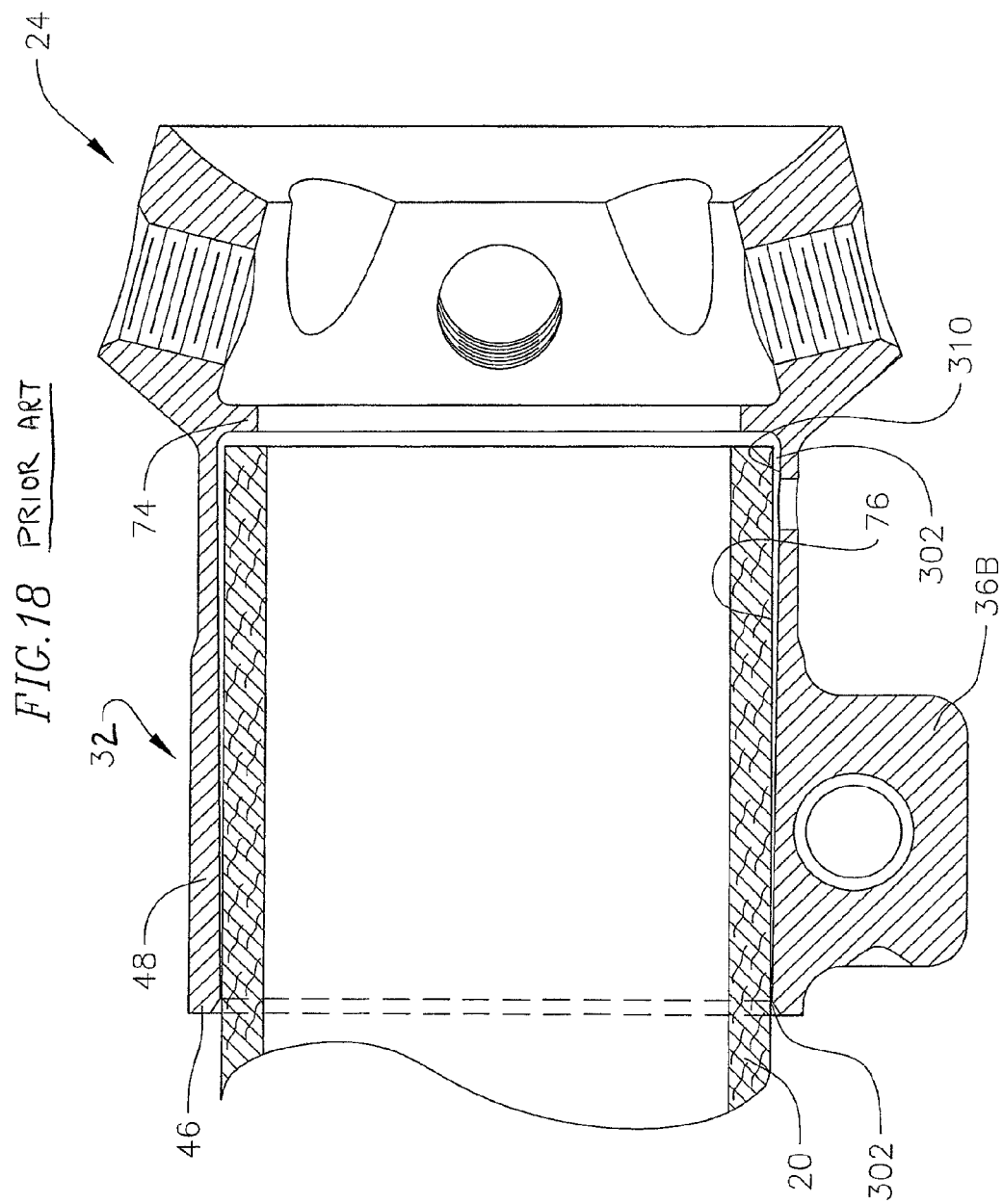
FIG. 18 is a cross-sectional view of the prior art tube clamp clamped on the tube through view lines 18-18 of FIG. 16.

FIG. 2 is a perspective view of a prior art tube clamp 24 and FIG. 3 is a bottom plan view of the prior art tube clamp of FIG. 2. It has a frustum receiving head region 30, and a clamping portion 32. A slot 34 is formed through the sidewall 48 of the clamping portion 32 and extends between two ears 36A and 36B. A bolt 42 will pass through an enlarged hole 38 in ear 36A and be threaded into ear 36B which has a threaded hole 40. At the frustum receiving head region 30 a bore 60 is formed therein, and four treaded holes 62 are formed through a perimeter thereof. As best shown in FIG. 18, the threaded holes 62 are tilted downwardly, and are adapted to receive Allen bolts 78 (shown in FIG. 3) which will project into the bore 60 and are used to retain a frustum head of a pyramid plug 450 such as shown in FIG. 22. The frustum receiving head region 30 has a top end 66 at the entrance of the bore 60. A cupped rim 68 is formed at the mouth of the bore 60 and narrows going into the bore 60. The cupped rim 68 is adapted to act as a seat for a spheroidal base region 452 of the pyramid plug 450 and allows the pyramid plug 450 to be swiveled relative to the tube clamp 24. As can be seen, the cupped rim 68 is fairly deep and extends from the top end 66 of the entrance of the bore 60 down to termination edge 70, and provides for a great abundance of contact surface with the spheroidal base region 452 of the pyramid plug 450. From the termination edge 70 the bore 60 widens downwardly to a bottom edge 72, where a collar 74 is formed. The volume in the bore 60 between the termination edge 70 and the bottom edge 72 is generally frustum shaped, and is adapted to receive a four sided frustum plug 454 of the pyramid plug 450 In the clamping portion 32, a central bore 44 is formed, having a smooth walled inside surface 76. When the tube 20 is inserted in the central bore 44, the end of the tube 20 will be prevented from traveling further inward by making contact with the collar 74.

As shown in FIG. 3, when tightened, the bolt 42 will cause the two ears 36A and 36B to be pulled together by virtue of the slot 34 and reduce the inner diameter "d" of the central bore 44 of the clamping portion 32. In prior art designs, the tightening of the bolt 42 tends to squeeze the bottom end 46 of the lower clamping portion 32 more than an upper end of the clamping portion 32 near a terminating end 40 of the slot 34. Thus, the majority of the reduction in diameter "d" of the central bore 44 occurs near the bottom end 46 of the clamping portion 32. In prior art tube clamps 32, the slot 32 is formed straight through the ears 36A and 36B and has the same width at the terminating end 48 as at the bottom end 46. Thus, there are cases where the ears 36A and 36B will touch each other when clamped. The ears 36A and 36B are generally evenly sized and shaped with similar amounts of material formed above the sidewalls 48. This large amount material of the ears 36A and 36B can make the sidewalls 48 in the region of the ears excessively rigid and can impede movement of the sidewalls, and thus interfere with reduction of the diameter "d" of the central bore 44 when the bolt 42 is tightened. Some additional shortcomings of the prior art design of tube clamp 24 are discussed further below.

Figure 4:
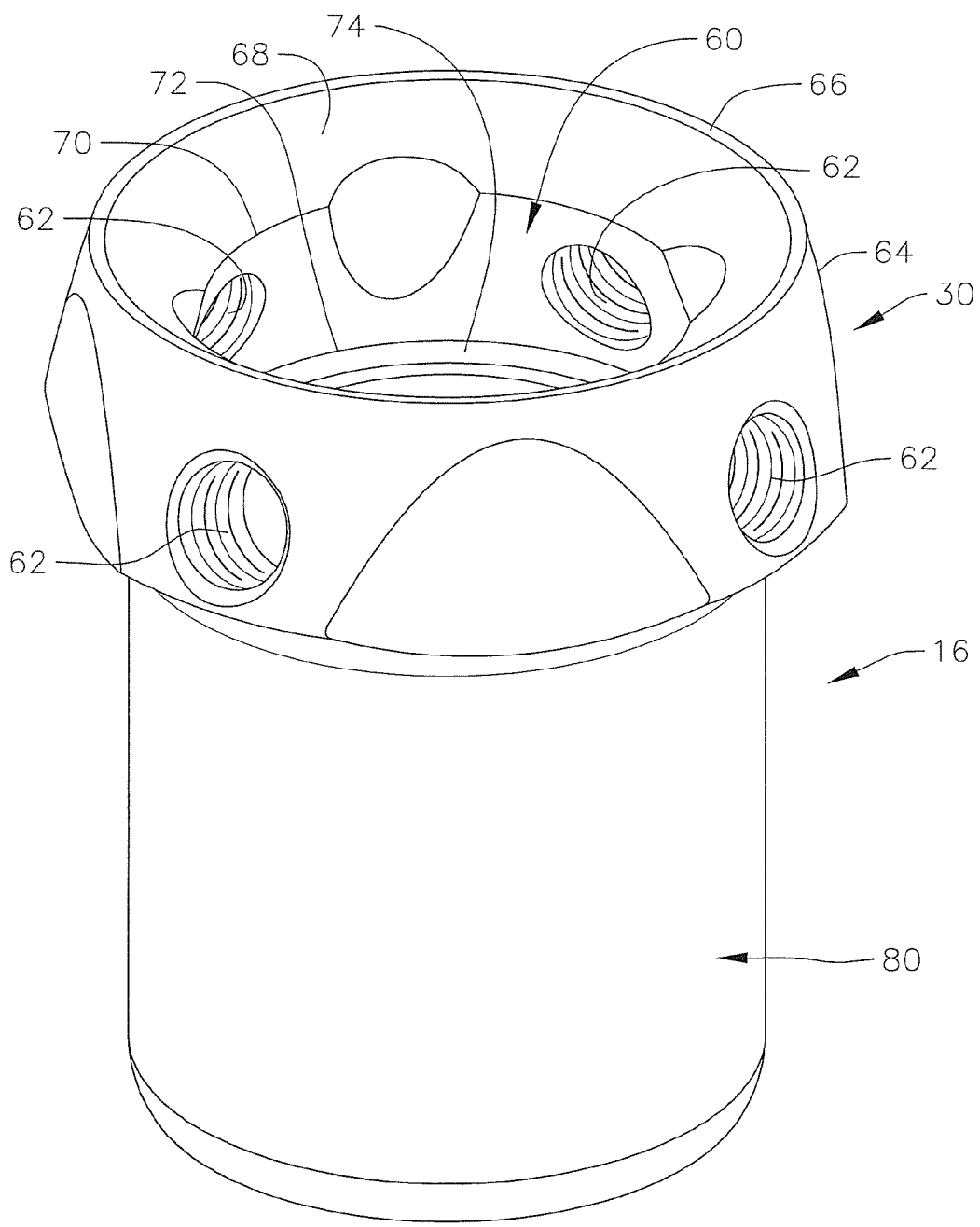
FIG. 4 is a perspective view of a prior art receiver.
Figure 5:
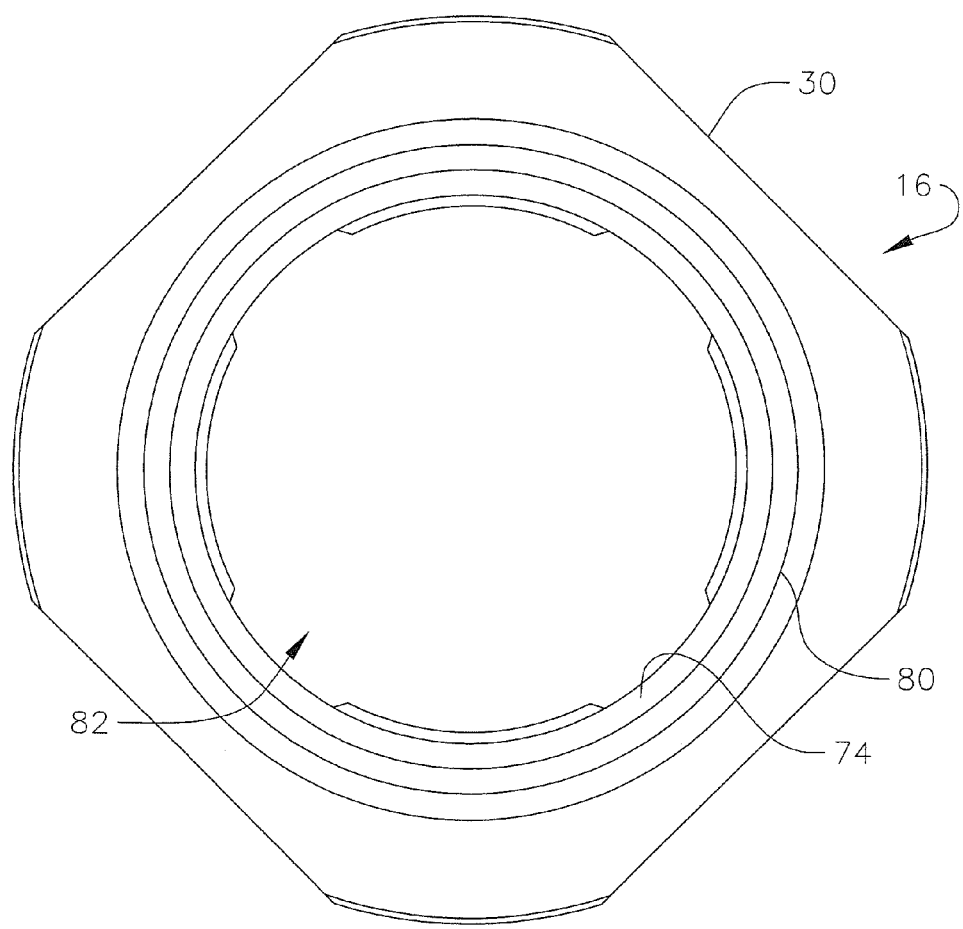
FIG. 5 is a bottom plan view of the prior art receiver of FIG. 4.
Figure 16:
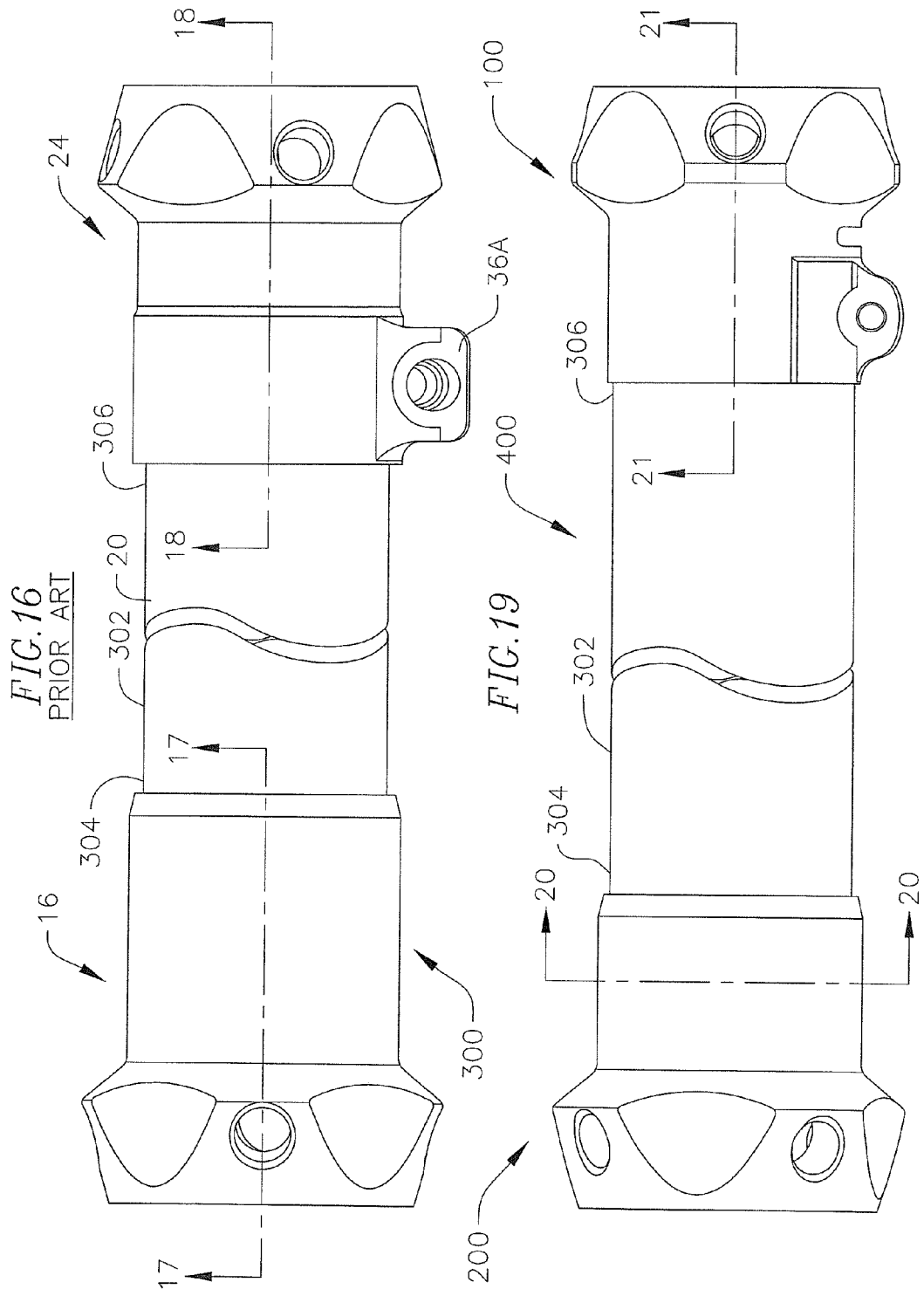
FIG. 16 is a side view of a prior art tube clamp assembly with a prior art receiver of FIG. 4 adhered to a first end of the tube and the prior art tube clamp of FIG. 2 clamped to the second end of the tube.
Figure 17:
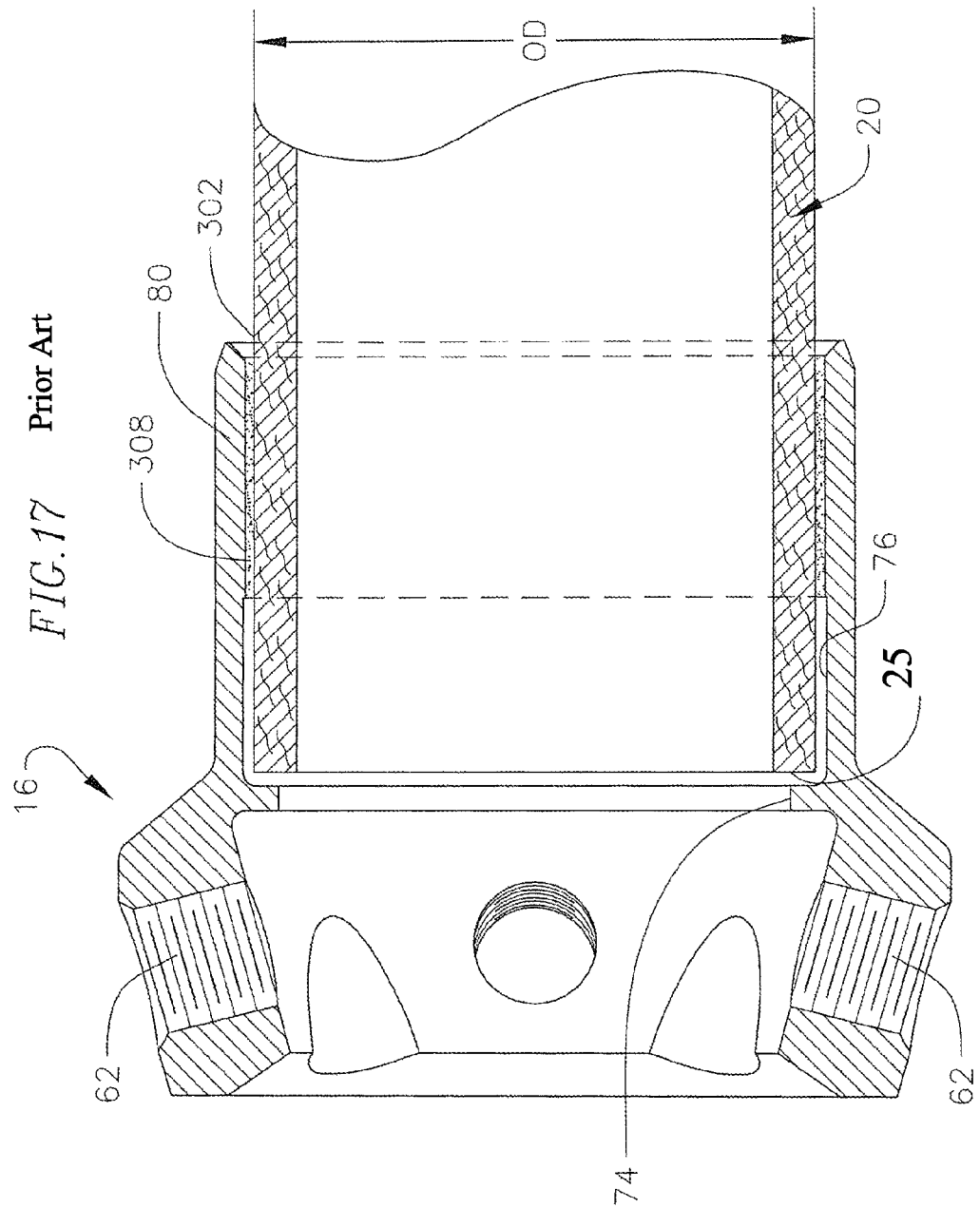
FIG. 17 is a cross-sectional view of the prior art receiver glued to the tube through view lines 17-17 of FIG. 16.

FIG. 4 is a perspective view and FIG. 5 is a bottom plan view of a prior art receiver 16 which is similar to the prior art tube clamp 24 of FIGS. 2, 3 and 18, and like reference numerals are used to refer to both prior art component. The prior art receiver 16 has a frustum receiving head region 30, and has a lower tube engagement portion 80 which has a central bore 82 At the frustum receiving head region 30 a bore 60 is formed therein, and four treaded holes 62 are formed through a perimeter 64 thereof. The threaded holes 62 are tilted downwardly, and are adapted to receive Allen bolts (shown in FIG. 3) which will project into the bore 60 and are used to retain a frustum head of a pyramid plug 450, such as shown in FIG. 22. The frustum receiving head region 30 has a top end 66 at the entrance of the bore 60. A cupped rim 68 is formed at the mouth of the bore 60 and narrows going into the bore 60. The cupped rim 68 is adapted to act as a seat for a base region 452 of the pyramid plug 450 and allows the pyramid plug 450 to be swiveled relative to the receiver 16. As can be seen, the cupped rim 68 is fairly deep and extends from the top end 66 of the entrance of the bore 60 down to termination edge 70, and provides for a great abundance of contact surface with the base region 454 of the pyramid plug 450. From the termination edge 70, the bore 60 widens downwardly to a bottom edge 72, where a collar 74 is formed. The volume in the bore 60 between the termination edge 70 and the bottom edge 72 is generally frustum shaped, and is adapted to receive the four sided frustum 454 of the pyramid plug 450. The tube engaging portion 80 is below the collar 74 and is sized to slip over a tube 20 and be glued thereto as shown in FIG. 16. The inside surface 76 of the bore 82 is smooth walled as shown in FIG. 17. When the tube 20 is inserted in the bore 82, the end of the tube 20 will be prevented from traveling further inward by making contact with the collar 74. A key difference between the tube clamp and the receiver 16 is that it includes neither a slot nor ears that are tightened with a bolt. The prior art receiver 16 are adhered to a tube 20 by adhesive 308, such as epoxy, as shown in FIG. 17. An inner surface 76 of central bore 82 of receiver 16 is smooth, and generally the inner surface will be scuffed up and cleaned, e.g., with alcohol, as is the end of the tube to which the receiver 16 will be adhered. However, due to mismatches between the inner diameter "d" of the receiver, and the outer diameter "OD" of the tube 20, a relatively large gap can exist which must be filled with adhesive 308 if a reliable bond is to be formed. As noted above, with time, temperature fluctuations, repeated shock and vibrations, the adhesive bond 308 between the inside surface 76 of the receiver 16 and the outside surface 302 of the tube 20 can give way, resulting in rotation of the receiver 16 and tube 20 relative to each other.

Figure 6:
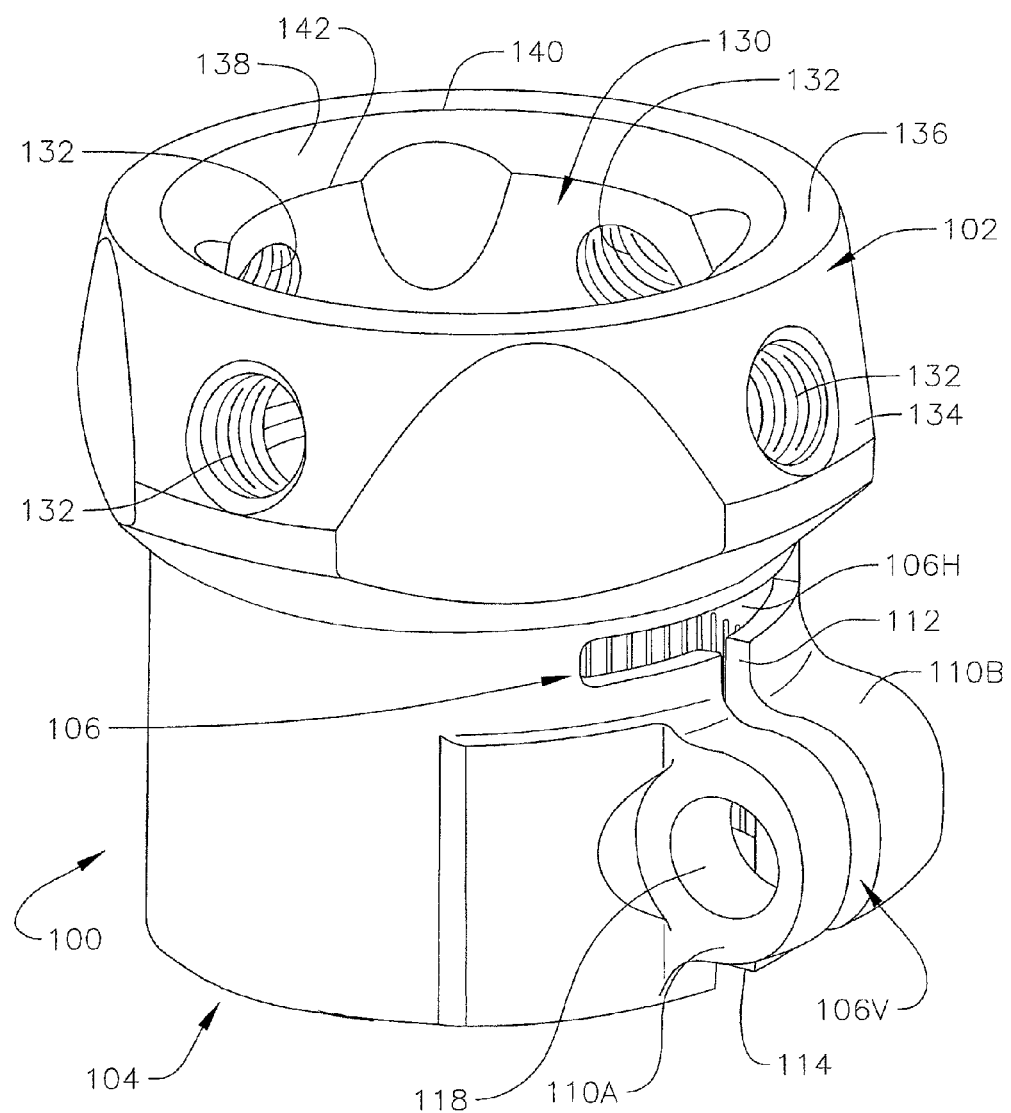
FIG. 6 is a perspective view of an exemplary embodiment of a tube clamp of the invention.
Figure 7:
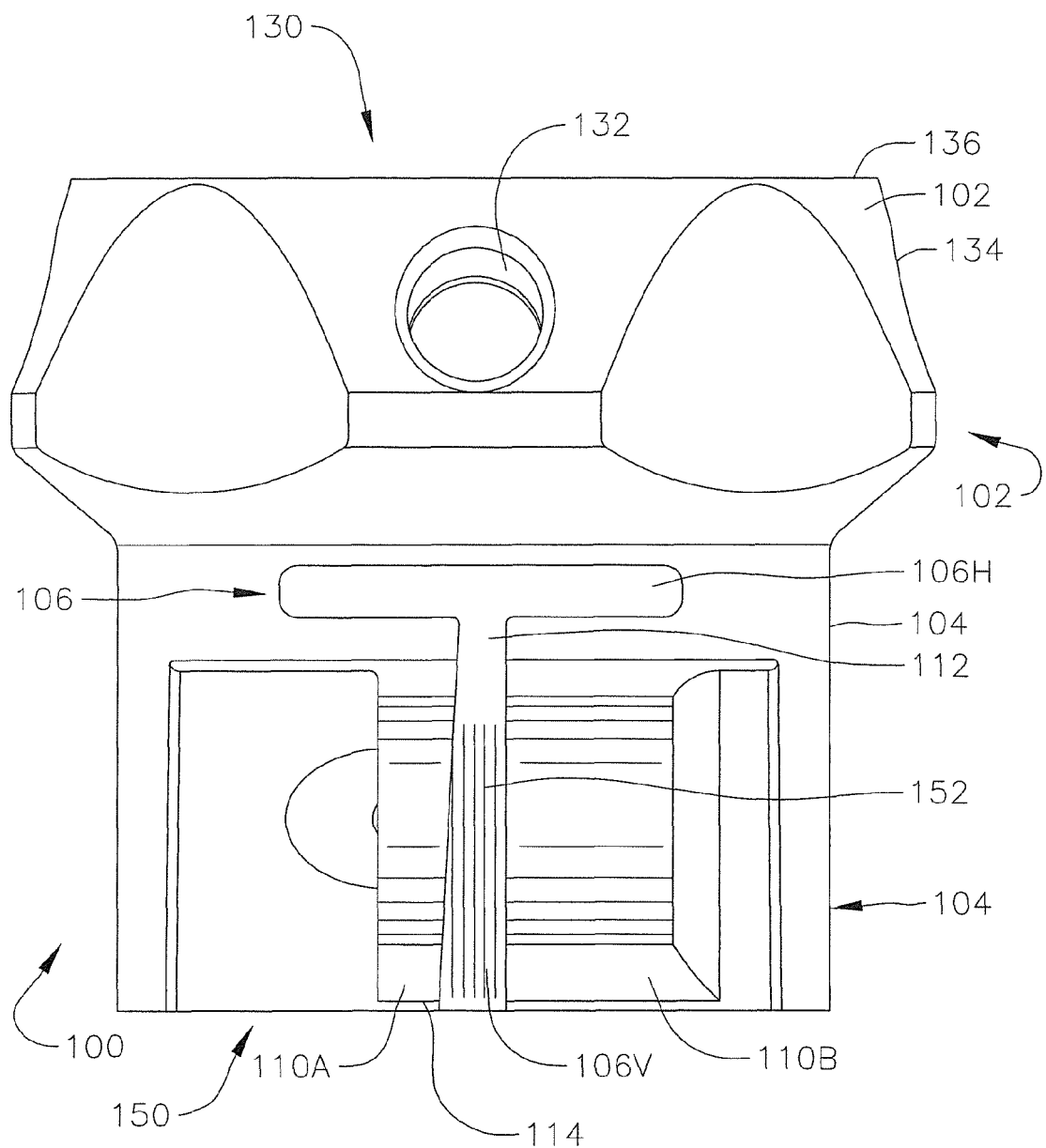
FIG. 7 is a front view of the tube clamp of FIG. 6.
Figure 8:
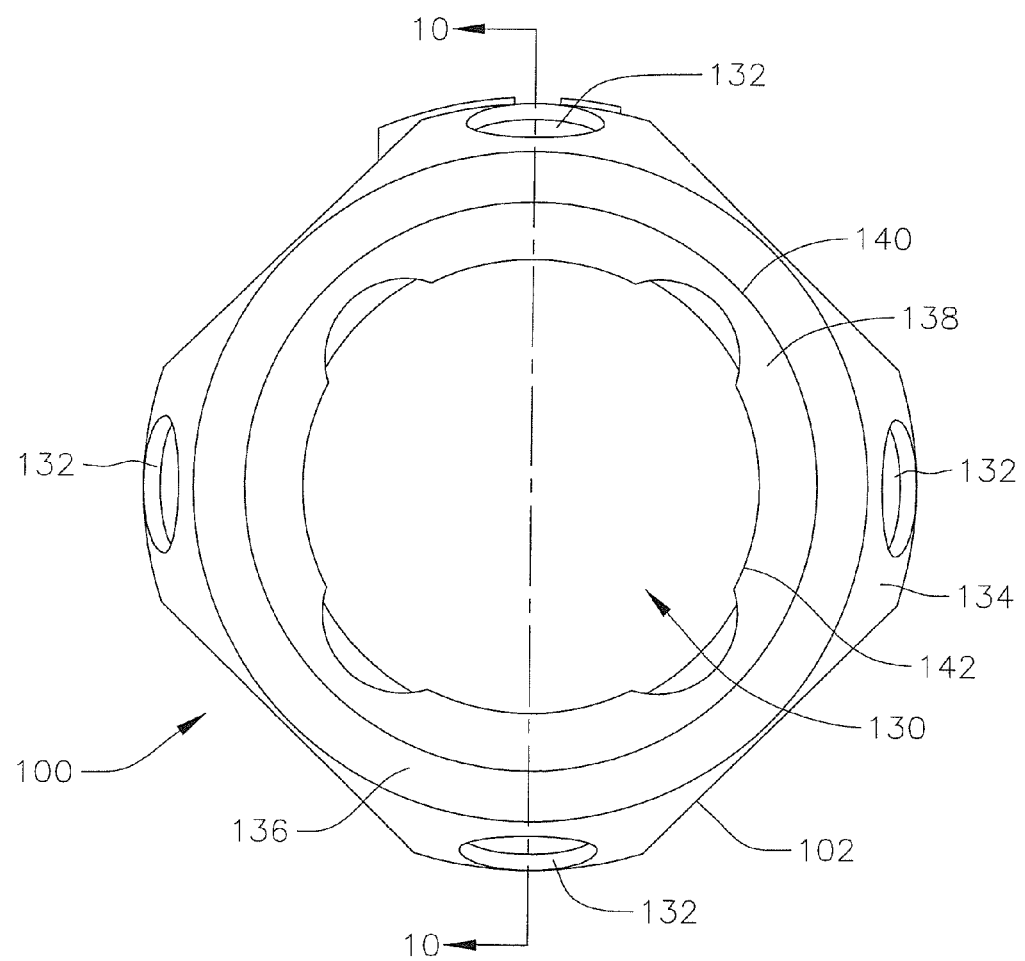
FIG. 8 is a top plan view of the tube clamp of FIG. 6.
Figure 9:
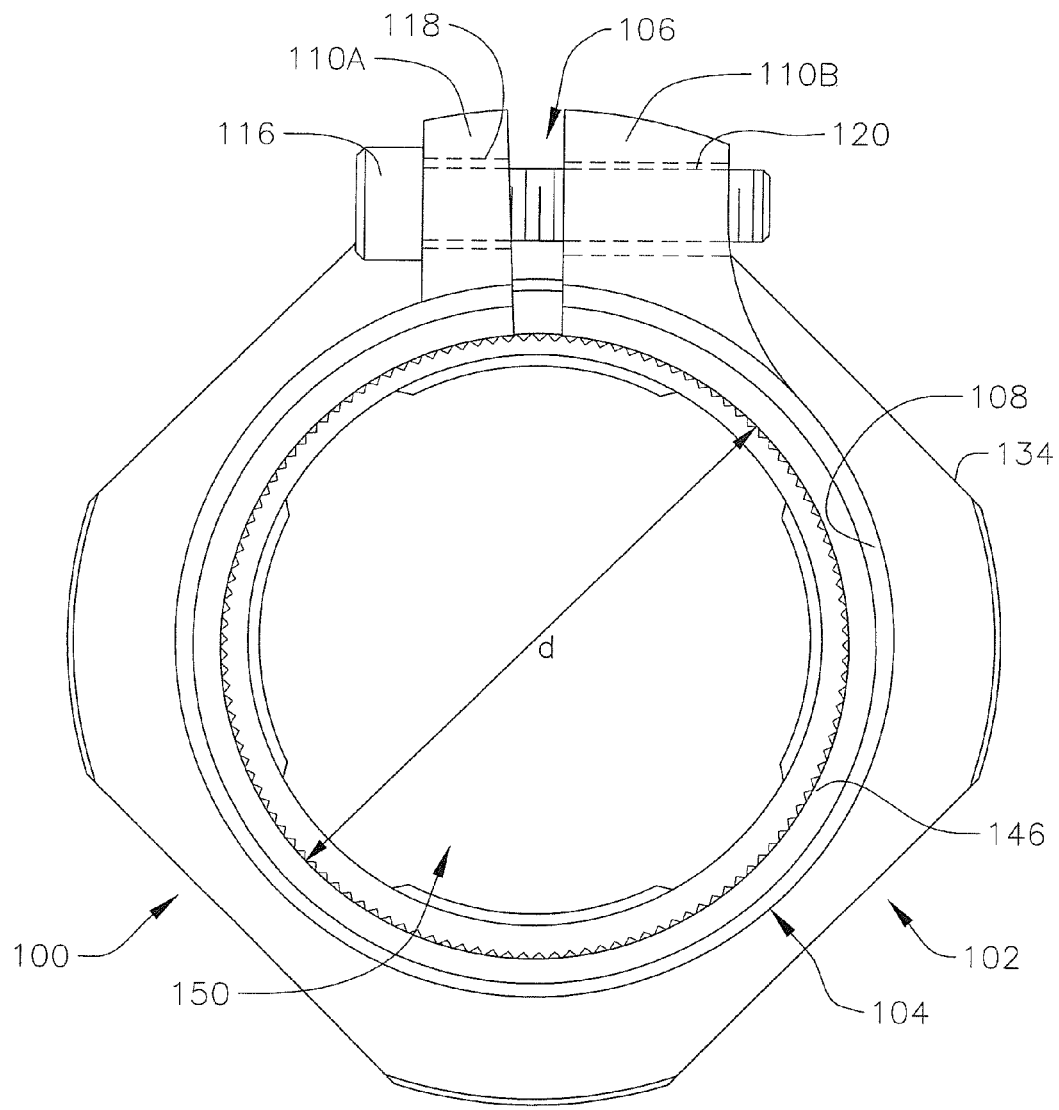
FIG. 9 is a bottom plan view of the tube clamp of FIG. 6 but with a screw.
Figure 10:
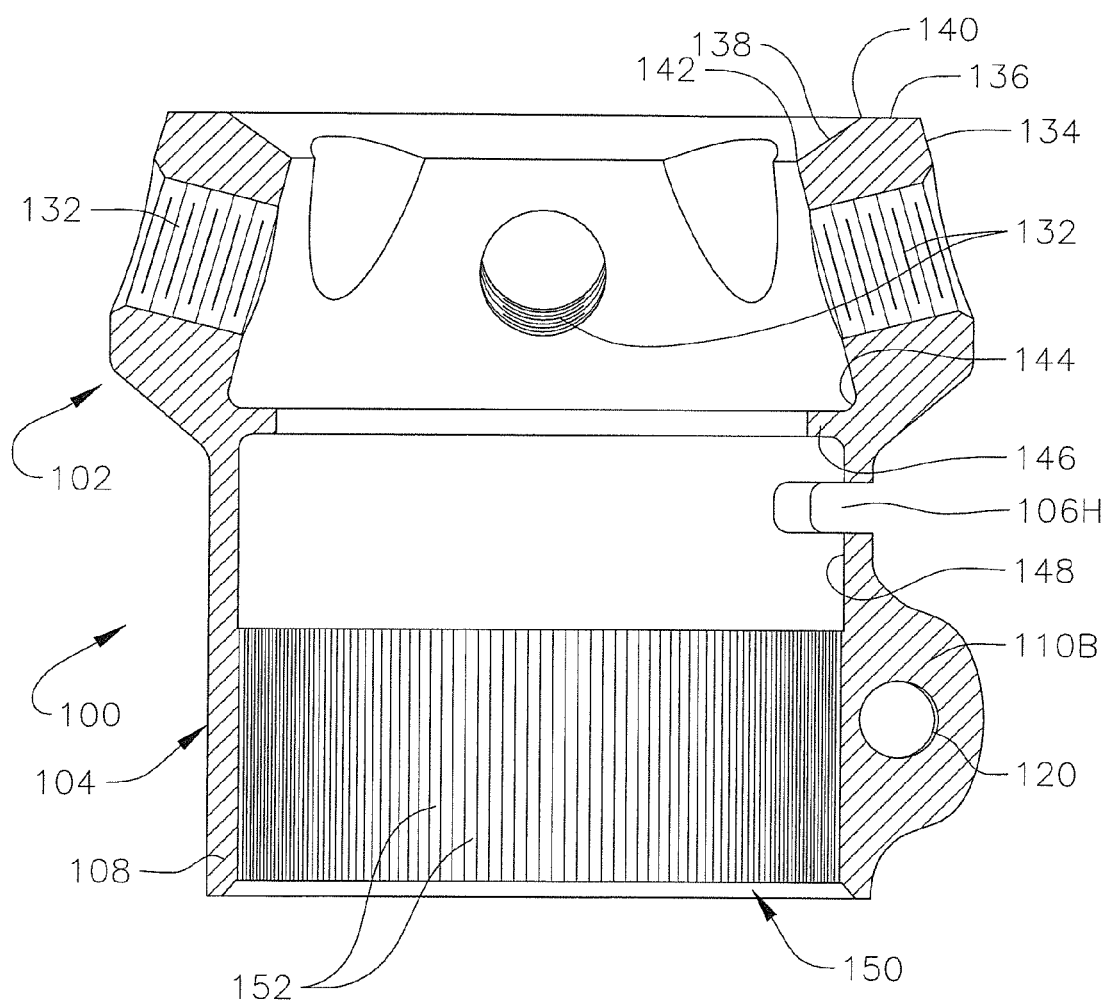
FIG. 10 is a cross-sectional view of the tube clamp of FIG. 6 through view lines 10-10 of FIG. 8.

FIG. 6 is a perspective view and FIG. 7 is a front view of an exemplary embodiment of a universal tube clamp 100 of the invention. FIG. 8 is a top plan view of the tube clamp 100 of FIG. 6, and FIG. 9 is a bottom plan view of the tube clamp 100 of FIG. 6. FIG. 10 is a cross-sectional view of the tube clamp 100 of FIG. 6 through view lines 10-10 of FIG. 8. The universal tube clamp 100 of the invention has a frustum receiving head portion 102, and a clamping portion 104 located below the head region 102. A generally T-shaped slot 106 is formed through a sidewall 108 of the clamping portion 104 and has a vertical slot section 106V that extends between two ears 110A and 110B and a horizontal slot section 106H that connects to an upper end 112 of the vertical section 106V. The vertical slot section 106V is preferably wider at its bottom 114 than at its upper end 112. A bolt 116 or other compression member (shown in FIG. 9) will pass through an enlarged hole 118 in ear 110A and be threaded into a threaded hole 120 in ear 110B. When the bolt 116 is tightened, it will cause the two ears 110A and 110B to be effectively moved together in the area of the slot 106V and thereby reduce an internal diameter "d" of the clamping portion 104.

In prior art tube clamps designs, such as shown in FIGS. 2 and 3, the ears 36A and 36B are generally evenly sized and shaped with similar amounts of material formed above the sidewalls 48, the sidewalls 48 in the region of the ears 36A and 36B can be excessively rigid and can impede, movement of the sidewalls, and thus interfere with reduction of the diameter "d" of the central bore 44 when the bolt 42 is tightened. Thus, tightening of the bolt 42 tends to squeeze just the bottom end 46 of the lower clamping portion 32 more than an upper end of the clamping portion 32 near the terminating end 49 of the slot 34. Moreover, in prior art tube clamps 32 shown in FIGS. 2 and 3, the slot 32 is formed straight through the ears 36A and 36B and has the same width at the terminating end 49 as at the bottom end 46. As noted above, the tolerances of tubes and tube clamps from different manufacturers often widely vary, and therefore, tube clamps are often oversized in their inner diameter and fit loosely on the ends of tubes. When this occurs, the prosthetist must tightened the bolt excessively, and there are cases where inner surfaces of the ears 36A and 36B will touch each other and prevent further tightening. Thus, in prior art designs, the majority of the reduction in diameter "d" of the central bore 44 occurs near the bottom end 46 of the clamping portion 32 and the area of contact between the tube clamp 24 on a tube 20 is minimum.

In contrast with the prior art design of tube clamps, the tube clamp 100 of the invention provides for a much more effective clamping action by virtue of the generally T-shaped slot 106 formed through the sidewall 108. Firstly, by providing a vertical slot section 106V that is preferably wider at its bottom 114 than at its top 112, greater reduction in the inner diameter "d" of the tube clamp 100 can take place before there is contact of the inner sides of the ears 110A and 110B of the slot 106. Moreover, the horizontal slot section 106H allows the areas of the clamping portion 104 below the horizontal slot section 106H to be displaced more readily, even areas that are further up on the clamping portion 104, and with less force and thus there can be greater reduction in the internal diameter "d". Lastly, by providing ear 110A having a smaller profile and with less material merging with the sidewall 108, the portion of the sidewall in the area of the ear 110A is less rigid and moves more when the bolt 116 is tightened into the threaded hole 120 in ear 110B. If desired, ear 110B can also be made to have less bulk so that that area of the sidewall 108 on the opposition side of the vertical slot section 106V will also be displaced more readily.

At the frustum receiving head region 102 a central bore 130 is formed therein, and four threaded holes 132 are formed through a perimeter 134 thereof. As best shown in FIG. 10, the threaded holes 132 are tilted downwardly, and are adapted to receive Allen bolts (not shown) which will project into the bore 130 and are used to retain a frustum head 454 of a pyramid plug 450, such as shown in FIG. 22. The frustum receiving head region 102 has a top end 136 at the mouth of the central bore 130. A cupped rim 138 is formed at the mouth of the central bore 130 and narrows going into the central bore 130. The cupped rim 138 is adapted to act as a seat for a base region 452 of the pyramid plug 450, and allows the pyramid plug 450 to be swiveled relative to the tube clamp 100. As can be seen, unlike the cupped rim 68 of the prior art tube clamp 24 of FIG. 2, the cupped rim 138 of the invention does not extend to the perimeter 134 of the frustum receiving head region 102, but instead stops short and thus there is a relatively large flat top end 136. The cupped rim 138 extends from an edge 140 on the top end 136 of the mouth of the central bore 130 down to termination edge 142 inside the central bore 130, and provides for adequate contact surface with the base region 452 of the pyramid plug 450. From the termination edge 142 of the cupped rim 138, the central bore 130 widens downwardly to a bottom edge 144, where a collar 146 is formed. The volume in the bore 130 between the termination edge 142 and the bottom edge 144 is generally frustum shaped, and is adapted to receive the four sided frustum 454 of the pyramid plug 450. Unlike the tube clamp 24 of the prior art, an inside surface 148 of a bore 150 of the clamping portion 104 has knurls 152 formed thereon. These knurls 152 are preferably formed vertically oriented on the inside surface 148 of the sidewall 108. As shown in FIG. 10, the knurls 152 are formed on the lower portion of the inside wall 148 below the horizontal slot portion 106H. Using the example of the setup shown in FIG. 1, when the clamping portion 104 is clamped on the tube 20, the tube 20 will be prevented from traveling further inward into the bore 150 by making contact with the collar 146, and the knurls 152 will mechanically "bite into" the outer surface of the tube 20, and help prevent the tube 20 from being rotated relative to the universal tube clamp 100.

Industry standards for the tube clamp I.D finish is between 32μ-64μ. A fixed, non-rotating position of the tube clamp and pylon relies on the tight tolerance between the I.D tube clamp and O.D pylon. There is minimal friction between the tube clamp I.D and pylon O.D due to the high surface finish of the pylon O.D (Aluminum and Carbon) and the standard I.D finish of the tube clamp. Rotating eventually occurs due to this discrepancy. The knurls in the inventor's tube clamp penetrate the surface of aluminum and/or carbon tubes; thus, preventing rotation.

Figure 11:
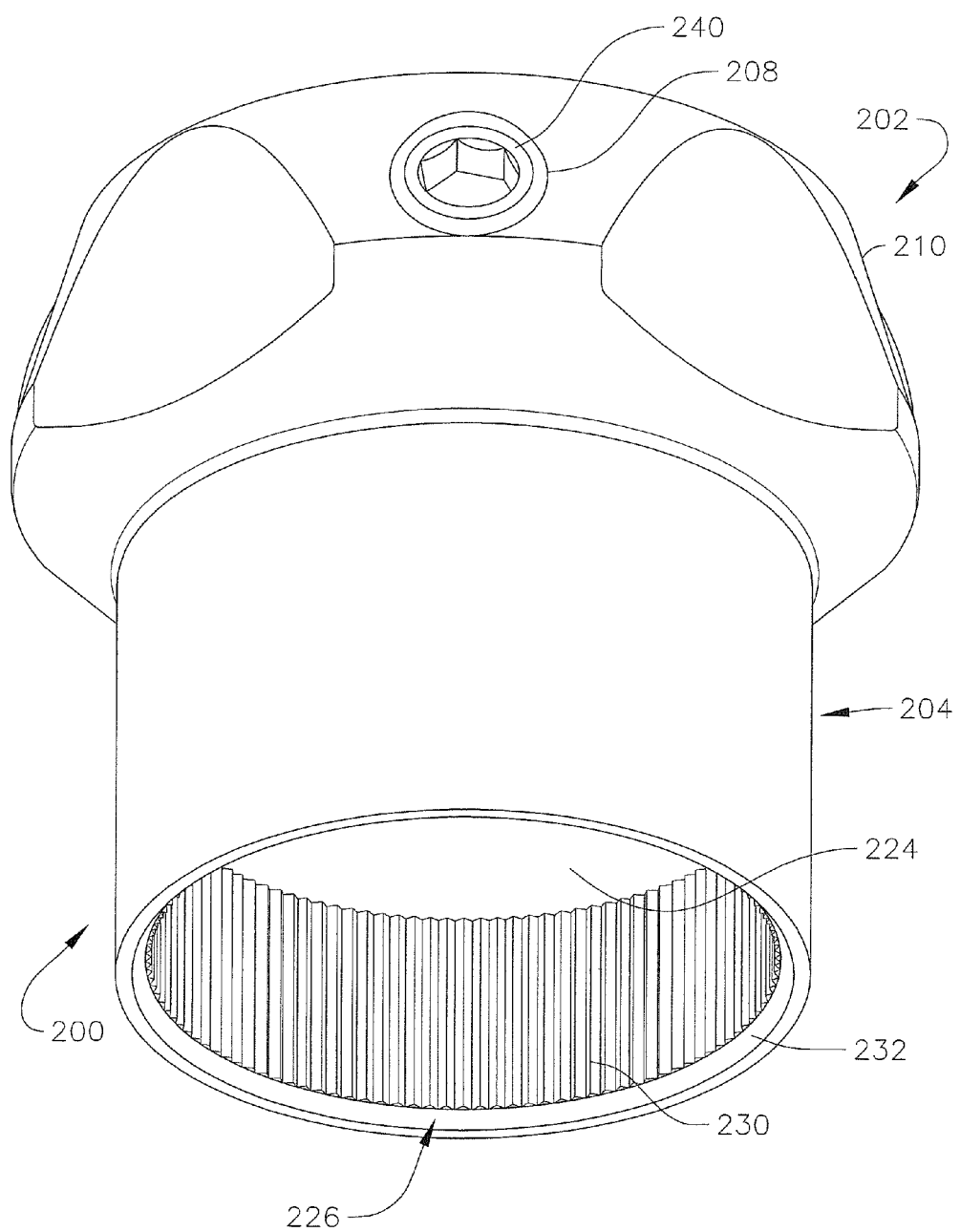
FIG. 11 is a perspective view of an exemplary embodiment of a receiver of the invention which is adapted to be permanently attached to an end of a tube.
Figure 12:
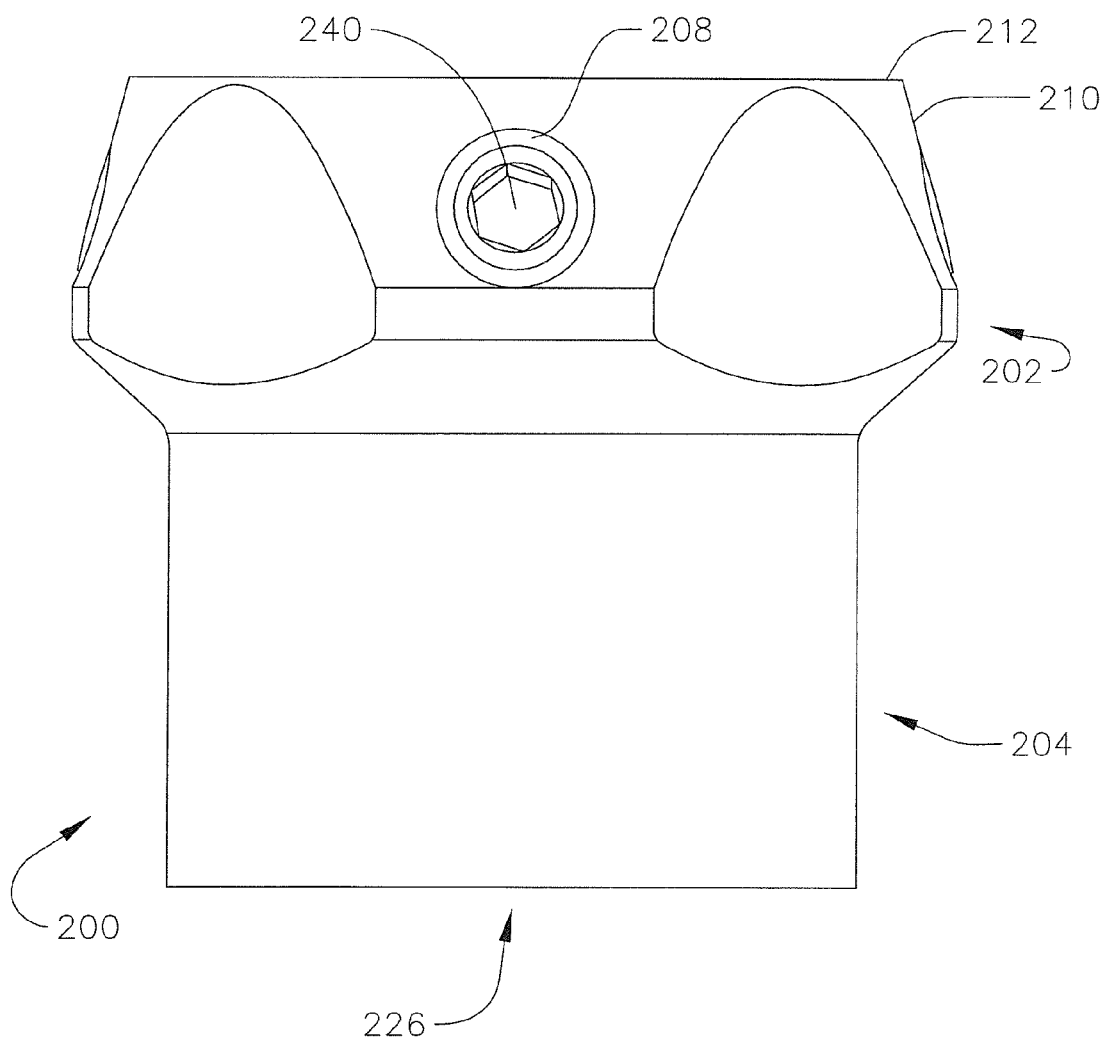
FIG. 12 is a front view of the receiver of FIG. 11.
Figure 13:
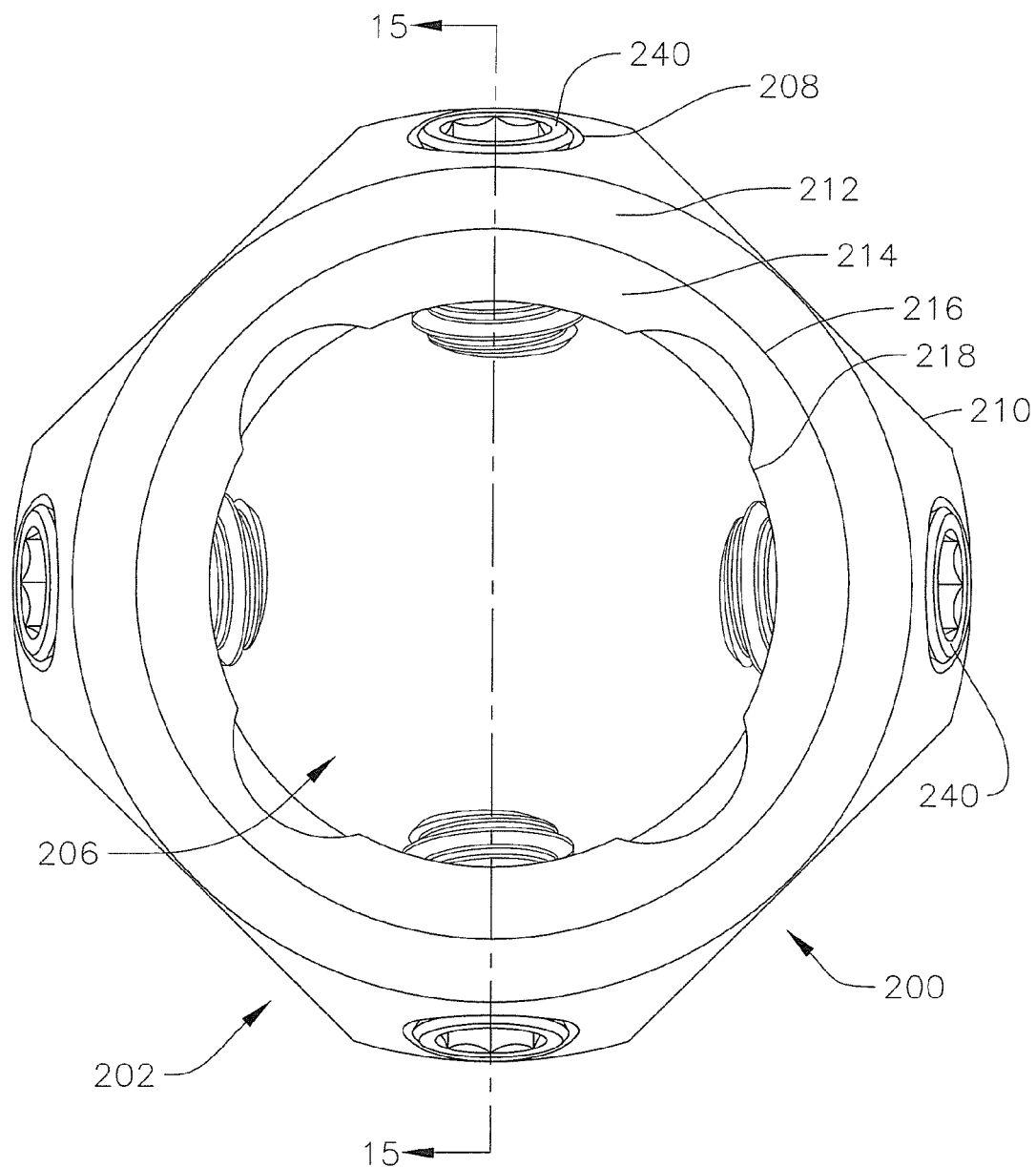
FIG. 13 is a top plan view of the receiver of FIG. 11.
Figure 14:
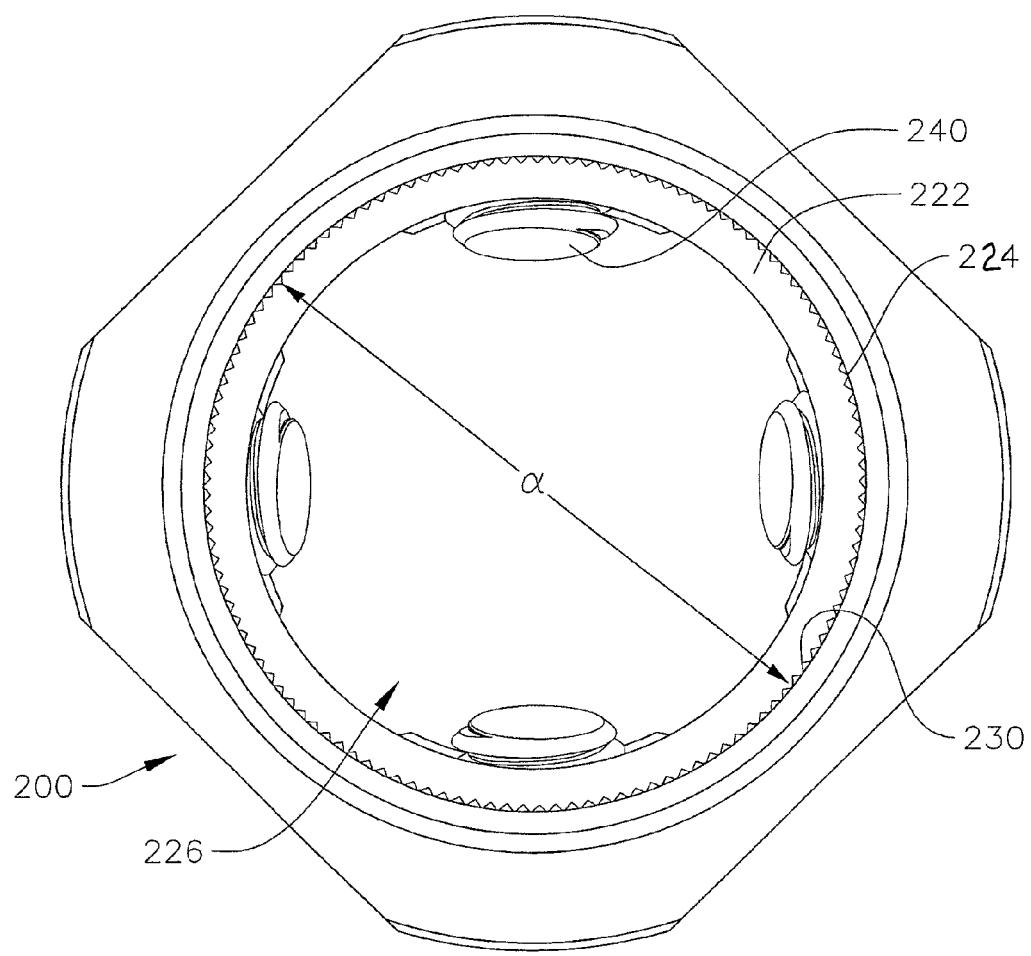
FIG. 14 is a bottom plan view of the receiver of FIG. 11.
Figure 15:
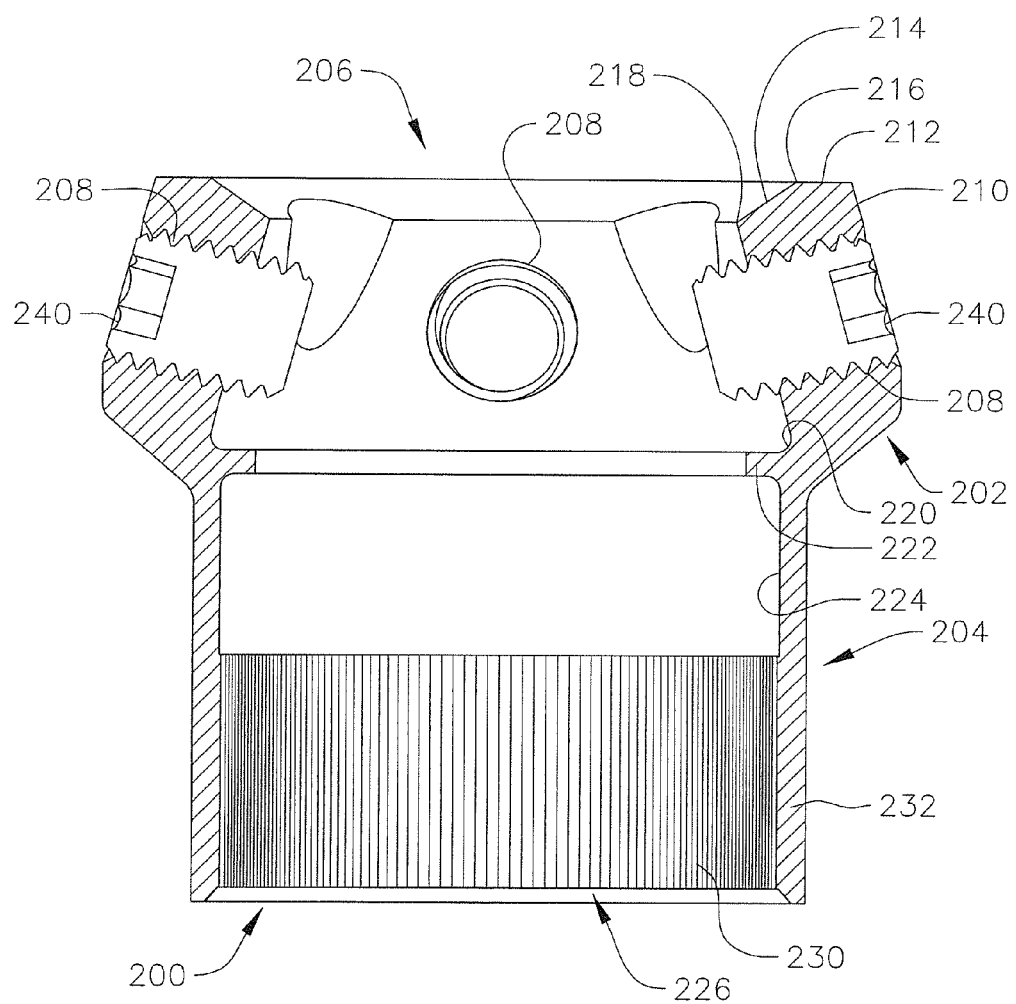
FIG. 15 is a cross-sectional view of the receiver through view lines 15-15 of FIG. 13.

FIG. 11 is a perspective view and FIG. 12 is a front view of an exemplary embodiment of a receiver 200 of the invention which is adapted to be permanently attached to an end of a tube, as shown in FIG. 19, FIG. 13 is a top plan view and FIG. 14 is a bottom plan view of the receiver 200. FIG. 15 is a cross-sectional view of the receiver 200 through view lines 15-15 of FIG. 13. The receiver 200 of the invention has a frustum receiving head portion 202, and a lower tube engaging portion 204 located below the head region 202. At the frustum receiving head region 202 a central bore 206 is formed therein, and four treaded holes 208 are formed through a perimeter 210 thereof. As best shown in FIG. 15, the threaded holes 208 are tilted downwardly and are adapted to receive alien bolts 240 which will project into the bore 206 and are used to retain a frustum head 454 of a pyramid plug 450 such as shown in FIG. 22. The frustum receiving head region 202 has a top end 212 at the mouth of the central bore 206. A cupped rim 214 is formed at the mouth of the central bore 206 and narrows going into the central bore 206. The cupped rim 214 is adapted to act as a seat for a spheroidal base region 452 of the pyramid plug 450 and allows the pyramid plug 450 to be swiveled relative to the receiver 200. As can be seen, unlike the cupped rim 68 of the prior art tube clamp 24 of FIG. 2, the cupped rim 214 of the invention does not extend to the perimeter 210 of the frustum receiving head region 202, but instead stops short and thus there is a relatively large flat top end 212. The cupped rim 214 extends from an edge 216 on the top end 212 of the mouth of the central bore 206 down to termination edge 218 inside the central bore 206, and provides for adequate contact surface with the spheroidal base region 452 of the pyramid plug 450 From the termination edge 218 of the cupped rim 214, the central bore 206 widens downwardly to a bottom edge 220, where a collar 222 is formed. The volume in the bore 206 between the termination edge 218 and the bottom edge 220 is generally frustum shaped, and is adapted to receive the four sided frustum plug 454 of the pyramid plug 450. Unlike the prior art receiver 16 of FIG. 4, in the receiver 200 the inside surface 224 of the bore 226 of the tube receiving portion 204 has knurls 230 formed thereon. These knurls 230 are preferably vertically oriented on the inside surface 224 of the sidewall 232.

FIG. 16 is a side view of a prior art tube clamp assembly 300 with a prior art receiver 16 of FIG. 4 adhered to an outside surface 302 of the tube 20 at a first end 304, and the prior art tube clamp 24 of FIG. 2 clamped to a second end 306 of the tube 20.

FIG. 17 is a cross-sectional view of the prior art receiver 16 glued to the tube 20 through view lines 17-17 of FIG. 16 with the end 25 of the tube 20 seated against the collar 74. The threaded holes 62 passing through the receiver at a slant are shown. As can be seen, adhesive 308 will be fill the space between the inside surface 76 of the sidewall 80 of receiver 16 and the outside surface 302 of tube 20. As previously noted, receivers and tubes of different manufacturers can vary widely in tolerances, and accordingly, the space between the sidewall 80 of receiver 16 and the outside of tube 20 can range from narrow to wide. As noted above, the tube can be made of materials including steel, aluminum, carbon fiber composite, and the receiver can be made of a different material, such as stainless steel, titanium, aluminum, and the receiver 16 and tube 20 can therefore have different coefficients of thermal expansion. Moreover, the adhesive joint is often subject to repeated stress and shock. As a result, the adhesive joint can fail.

FIG. 18 is a cross-sectional view of the prior art tube clamp 24 clamped onto an outer surface 302 of the tube 20 through view lines 18-18 of FIG. 16. Before the bolt (not shown) is tightened through the ears 36A and 36B (only ear 46B being shown), a gap 310 is present between the outer surface 302 of the tube 20 and the smooth walled inside surface 76 of the clamping portion 32. With the second end 306 of the tube 20 inserted in the central bore 44, the second end 306 of the tube 20 will be prevented from traveling further inward by making contact with the collar 74. When bolt (not shown) is tightened through the ears 36A and 36B (only ear 36B being shown), the gap 310 present between the outer surface 302 of the tube 20 and the smooth walled inside surface 76 of the clamping portion 32 will squeeze the bottom end 46 of the clamping portion 32 more than an upper end of the clamping portion 32 near a terminating end of the slot 34 (as shown in FIGS. 2 and 3). Thus, the majority of the reduction in diameter "d" of the central bore 44 occurs near the bottom end 46 of the clamping portion 32, and there is little if no surface contact between the outer surface 302 of the tube 20 and the smooth walled inside surface 76 of the clamping portion 32 except near a bottom of the clamping portion. Since the clamping portion 32 has a smooth walled inside surface 76, there is little bite between the clamping portion 32 and the tube 20. Lastly, as previously discussed with reference to FIGS. 2 and 3, tube clamps and tubes of different manufacturers can vary widely in tolerances, and accordingly, the space 310 between the sidewall 48 of tube clamp 24 and the outside surface 302 of tube 20 can range from narrow to wide so sometimes if the tube clamp 24 has central bore 44 with an oversized diameter d and the tube 20 has a smaller than average outer diameter, the width of the slot 34 is too narrow and the ears 36A and 36B contact before the tube clamp 24 can be sufficiently tightened on the outer surface 302 of the tube 20, and as a result, the tube clamp 24 and tube 20 can rotate relative to each other.

FIG. 19 is a side view of the art tube clamp assembly 400 of the invention with the exemplary receiver 200 of FIG. 11 secured to an outside surface 302 of the tube 20 at a first end 304, and the exemplary tube clamp 100 of FIG. 6 clamped to the second end 306 of the tube 20.

Figure 20:
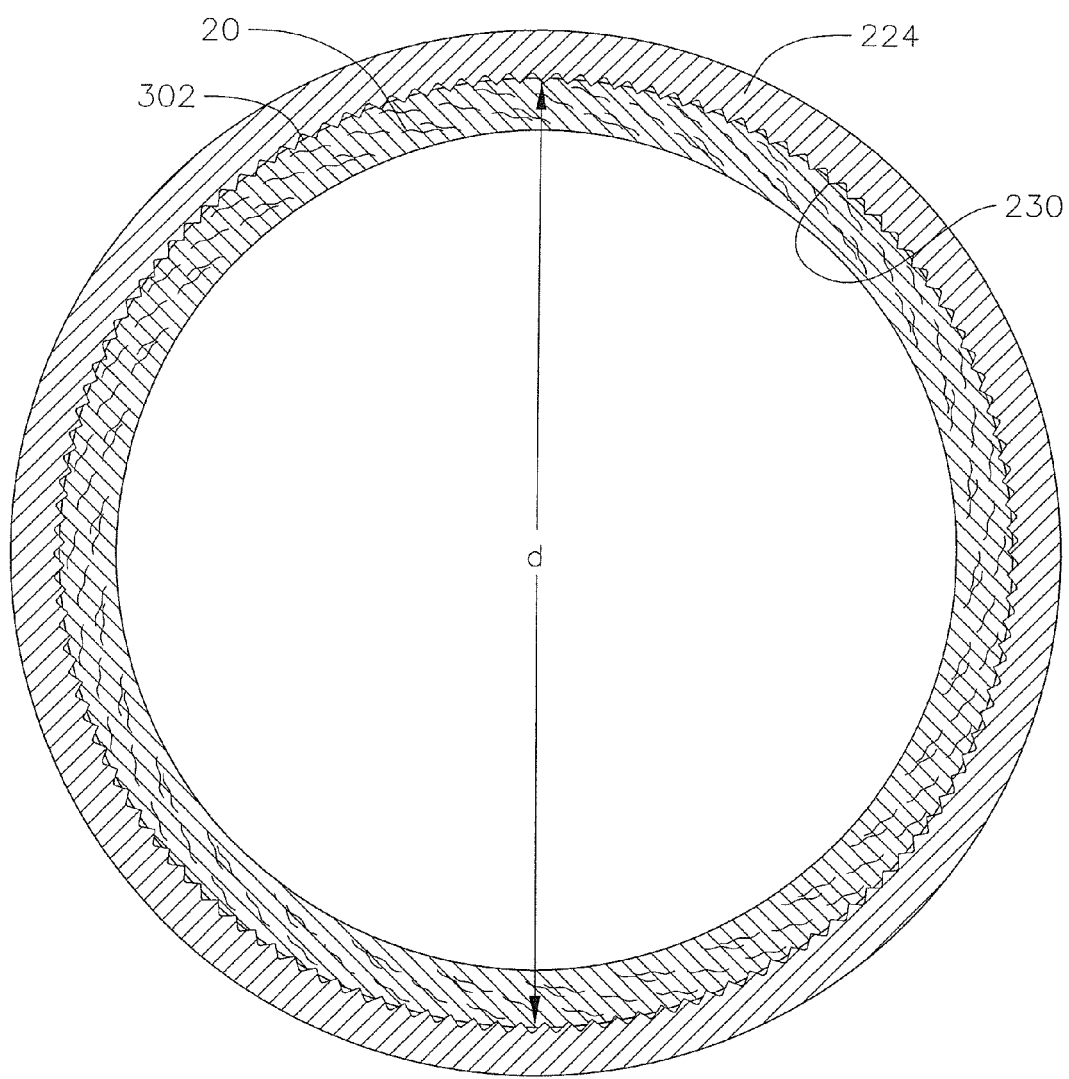
FIG. 20 is a cross-sectional view of the receiver fitted on the tube through view lines 20-20 of FIG. 19.

FIG. 20 is a cross-sectional view of the receiver 200 of FIG. 11 fitted on the tube 20 through view lines 20-20 of FIG. 19. The knurls 230 extend inwardly from inner walls 224 having a nominal diameter "d" and are sized proportioned to be provide a smaller inner diameter than expected outer diameter of tubes 20 of various manufacturers. In practice, the receiver 200 will be compressed or pounded onto the end 304 of the tube 20, and the knurls 230 will mechanically form furrows or gashes in the outer surface 302 of the tube 20, and help prevent the tube 20 from being rotated relative to the receiver 200, even in cases where the outer diameter of the tube is smaller than expected. The knurls 230 can have a variety of cross-sections shapes including but not limited to v-shaped points, rectangles, trapezoids. While the knurls 230 are showed continuous spaced inside the central bore but only at a lower end thereof, they can extend further up the central bore is desired.

Figure 21:
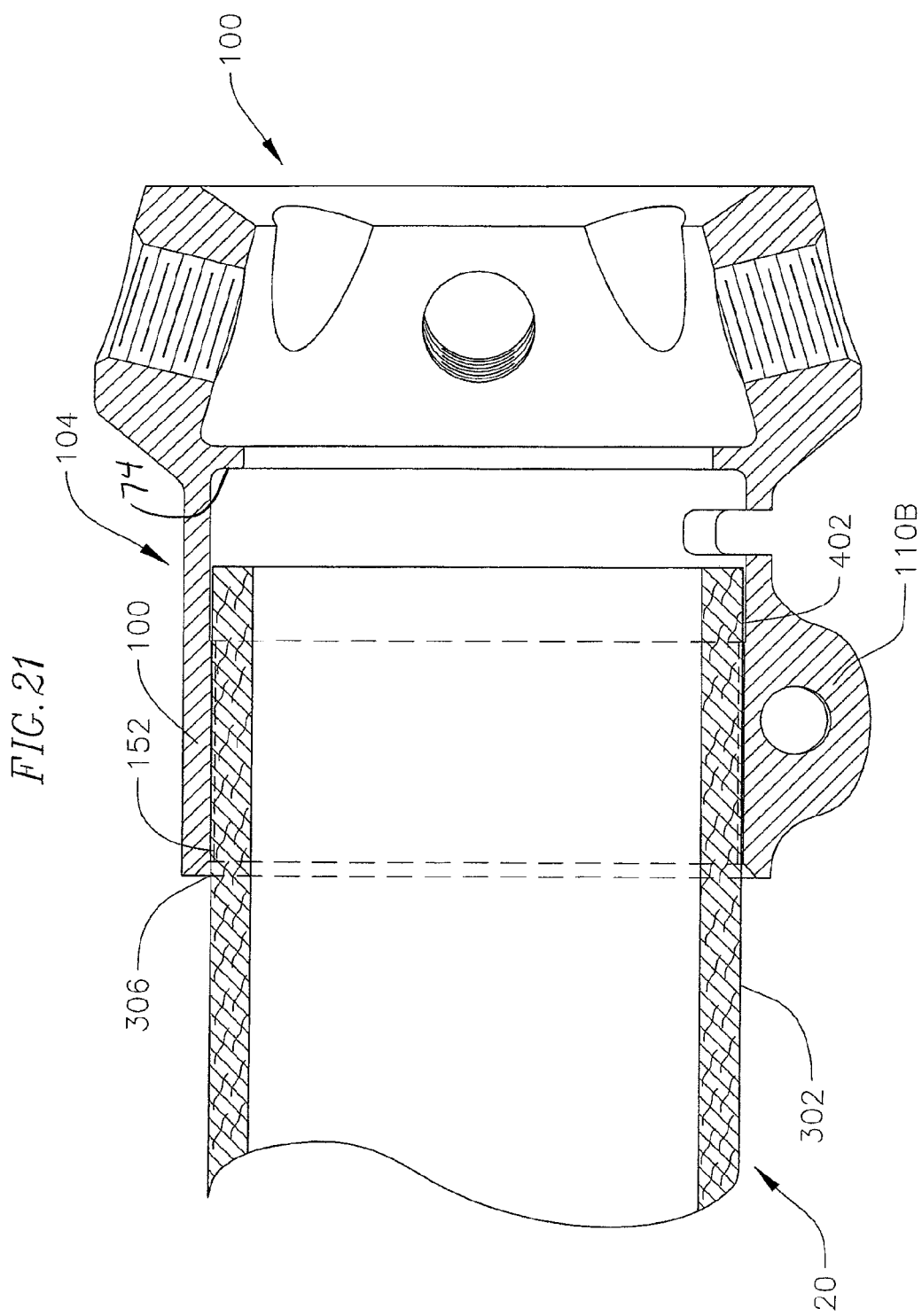
FIG. 21 is a cross-sectional view of the exemplary tube clamp clamped on the tube through view lines 21-21 of FIG. 19.

FIG. 21 is a cross-sectional view of the exemplary tube clamp 100 clamped on the tube 20 through view lines 21-21 of FIG. 19. Before the bolt (not shown) is tightened through the ears 110A and 110B (only ear 110B being shown), a gap 402 is present between the outer surface 302 of the tube 20 and the knurled walled inside surface 148 of the clamping portion 104. With the second end 306 of the tube 20 inserted in the central bore 150 (see FIG. 9), the second end 306 of the tube 20 will be prevented from traveling further inward by making contact with the collar 74. When bolt (not shown) is tightened through the ears 110A and 110B (only ear 110B being shown), the gap 310 present between the outer surface 302 of the tube 20 and the knurls 152 on the inside surface 148 of the clamping portion 104 will move inwardly regions of the clamping portion below the horizontal slot section 106H, and thus resulting in both a greater reduction in diameter "d" of the central bore 150 over more of the sidewall 108 compared to the prior art tube clamp 24, so that there will be greater contact between the outer surface 302 of the tube 20 and the knurls 152 on the inside surface 148 of the clamping portion 104. Moreover, by virtue of the vertical slot section 106H being wider at its bottom 114 than at its top 112, there can be greater movement of the sidewalls 108 compared to the prior art tube clamp 32. When the tube clamp is tightened, the knurls 152 will mechanically "bite into" the outer surface 302 of the tube 20, and help prevent the tube 20 from being rotated relative to the universal tube clamp 100. Before the bolt (not shown) is tightened through the ears 110A and 110B (only ear 110B being shown), a gap 402 is present between the outer surface 302 of the tube 20 and the knurled walled inside surface 148 of the clamping portion 104.

Referring to FIGS. 16 and 19, as can be seen by comparing the relative lengths of the prior art receiver 16 with the receiver 200 of the invention, and the prior art tube clamp 24 with the universal tube clamp 100 of the invention, the receiver 200 and the universal tube clamp 100 of the invention are substantially shorter in length than the prior art receiver 16 and prior art tube clamp 24, respectively. In cases were expensive material is used to manufacturer these components, e.g., titanium, this reduction in length (about 23%) results in less material be used, which substantially reduces material costs and weight of the finished product, while decreasing likelihood of failure.

FIG. 22 is a perspective view of a prior art pyramid plug 450 having a spheroidal base region 452 with a four sided frustum plug 454.

Having thus described the exemplary embodiments of the present invention, it should be understood by those skilled in the art that the above disclosures are exemplary only and that various other alternatives, adaptations, and modifications may be made within the scope of the present invention. The presently disclosed embodiment is to be considered in all respects as illustrative and not restrictive. The scope of the invention being indicated by the appended claims rather than the foregoing description, and all changes which come within the meaning and range of equivalency of the claims are, therefore, intended to be embraced therein.

What is claimed is:

1. A universal tube clamp for prosthetics, comprising:
a head portion with an aperture formed therein with set screws to retain another object thereto; and
a clamping portion, the clamping portion comprising an outer perimeter sidewall defining a generally cylindrical opening therein with knurls formed on inner surfaces of the sidewall, a generally T-shaped slot with a vertical portion and a horizontal slot portion, the vertical portion extends from a bottom of the sidewall upwardly towards the head portion with a first ear extending from the sidewall on a first side of the slot and a second ear extending from the sidewall on a second side of the slot, and the horizontal slot portion extends horizontally through the sidewall above the first ear and the second ear to allow for enhanced movement of the sidewall in the vicinity of the T-shaped slot, and a bolt which has a head which impinges on the first ear and a threaded end which threads into the second ear to selectively force the first and second ears together to reduce a diameter of the generally cylindrical opening and engage the knurls formed on the inner surfaces of the sidewall of the clamping portion with the tube being clamped, wherein the first ear is narrower than the second ear, wherein the vertical portion of the T-shaped slot is wider at the bottom of the sidewall than at a top of the slot where the vertical portion of the T-shaped slot joins the horizontal slot portion to allow for greater reduction in the diameter of the clamping portion near the bottom of the sidewall than at the top of the slot.

2. The universal tube clamp for prosthetics of claim 1, wherein the vertical portion of the T-shaped slot, cuts between the first and second ears and the slot is wider at an outer perimeter of the ears than where the vertical portion of the T-shaped slot passes through the sidewall.

3. The universal tube clamp for prosthetics of claim 1, wherein the head portion comprises a top surface and a narrow cupped bevel which extends downwardly and inwardly into the head portion towards the clamping portion, which cupped bevel is spaced away from an outer perimeter of the head portion.

4. The universal tube clamp for prosthetics of claim 1, wherein the knurls formed on the inner surfaces of the sidewall are oriented parallel to an axis of the clamping portion.

5. The universal tube clamp for prosthetics of claim 4, wherein the knurls formed on the inner surfaces of the sidewall are oriented parallel to an axis of the opening.

* * * * *